US000001929H

United States Statutory Invention Registration [19]

[11] Reg. Number: H1,929

Citak

[45] Published: Dec. 5, 2000

[54] CARDIAC RHYTHM MANAGEMENT SYSTEM WITH LEAD IMPEDANCE MEASUREMENT

[76] Inventor: Brian Citak, 6379 Crackleberry Bay, Woodbury, Minn. 55129-9529

[21] Appl. No.: 09/185,457

[22] Filed: Oct. 3, 1998

[51] Int. Cl.[7] ..... A61N 1/18

[52] U.S. Cl. ..... 607/28

[58] Field of Search ..... 607/8, 11, 19, 607/28

*Primary Examiner*—Harold J. Tudor

*Attorney, Agent, or Firm*—Schwegman, Lundberg, Woessner & Kluth, P.A.

[57] ABSTRACT

An implanted cardiac rhythm management device, such as a pacemaker (pacer) or defibrillator provides a lead impedance measurement of the effective resistance of the leadwire connecting the device to electrodes in the heart. The lead impedance measurement is based on the amount of a voltage droop of a capacitively coupled pacing output voltage pulse over a fixed period of time that is shorter than the duration of the pacing pulse. The lead impedance measurement avoids the need for performing a natural logarithm function by using a look-up table of precalculated scaled resistance values corresponding to particular amounts of voltage droop. The lead impedance measurement is enhanced by performing interpolation and correcting for manufacturing tolerances of the particular cardiac rhythm management device.

1 Claim, 5 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CARDIAC RHYTHM MANAGEMENT SYSTEM WITH LEAD IMPEDANCE MEASUREMENT

FIELD OF THE INVENTION

This invention relates generally to cardiac rhythm management systems and particularly, but not by way of limitation, to a cardiac rhythm management system with a lead impedance measurement circuit.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias is via drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire having one or more electrodes disposed in the heart. Heart contractions are initiated in response to such pace pulses. By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem that arises in cardiac rhythm management devices is in determining lead impedance, that is, the effective resistance of the leadwire that couples the cardiac rhythm management device to the heart for delivering the electrical pacing pulses at electrodes within the heart. The value of the lead impedance provides useful information. For example, an extremely low lead impedance value may indicate a short circuit between the pacing electrodes. An extremely large lead impedance value may indicate an open circuit such as, for example, resulting from a leadwire that has become disconnected from the cardiac rhythm management device. Both defective leadwire conditions must be detected and remedied if the cardiac rhythm management device is to provide effective pacing therapy to the heart.

It is possible to calculate lead impedance based on a measurement of voltage droop from a capacitively coupled pacing pulse delivered to the heart. However, a lead impedance measurement based on measured pacing voltage droop typically requires a complicated natural logarithm function, ln(), to be performed. Because of the difficulty associated with performing a complex natural logarithm function, ln(), there is a need for other techniques of measuring lead impedance that avoid performing a complex natural logarithm, ln( ), function.

SUMMARY

The present system provides a lead impedance measurement based on measured pacing voltage droop, but which does not require a complex natural logarithm function to be performed at the time of the lead impedance measurement. This allows the lead impedance measurement to be performed completely within an implanted cardiac rhythm management device that does not need to incorporate circuits for performing the natural logarithm function. Because lead impedance measurements can be made entirely within the implanted cardiac rhythm management device, there is no need to communicate data to an external programmer for performing a natural logarithm function and determining the lead impedance in the external programmer.

Because lead impedance is measured entirely within the cardiac rhythm management device, the cardiac rhythm management device is capable of automatically performing several desirable functions. In one embodiment, performing the lead impedance measurement entirely within the implanted cardiac rhythm management device allows the implantable device to perform an Exit Shipping State function. In one such example, the implantable cardiac rhythm management device is placed in a shipping state when shipped from a manufacturing facility. Upon detecting a substantial decrease in lead impedance (or an increase in voltage droop at the lead terminals) from the open-circuit condition in which it is shipped, the cardiac rhythm management device automatically exits the shipping state and begins delivering pacing pulses at nominal pacing conditions (e.g., VVI mode, 3.5 Volt and 0.4 millisecond pace pulses).

In another embodiment, performing the lead impedance measurement entirely within the implanted cardiac rhythm management device allows the device to perform an Auto Lead Configuration function. In one such example, the implanted cardiac rhythm management device automatically switches from bipolar pacing (i.e., delivering pacing pulses between electrodes that are both disposed on a distal tip of the leadwire in the heart) to unipolar pacing (i.e., delivering pacing pulses between an electrode disposed on the distal tip of the leadwire in the heart, and a second electrode located on the housing of the implanted cardiac rhythm management device implanted in the pectoral region or elsewhere). This allows pacing pulses to continue to be provided from a good electrode in the heart if the other electrode in the heart becomes disconnected from the cardiac rhythm management device, such as by a break in the leadwire connecting that electrode to the cardiac rhythm management device.

BRIEF DESCRIPTION OF THE DRAWINGS

In the drawings, like numerals describe substantially similar components throughout the several views.

DETAILED DESCRIPTION

Figure 1:
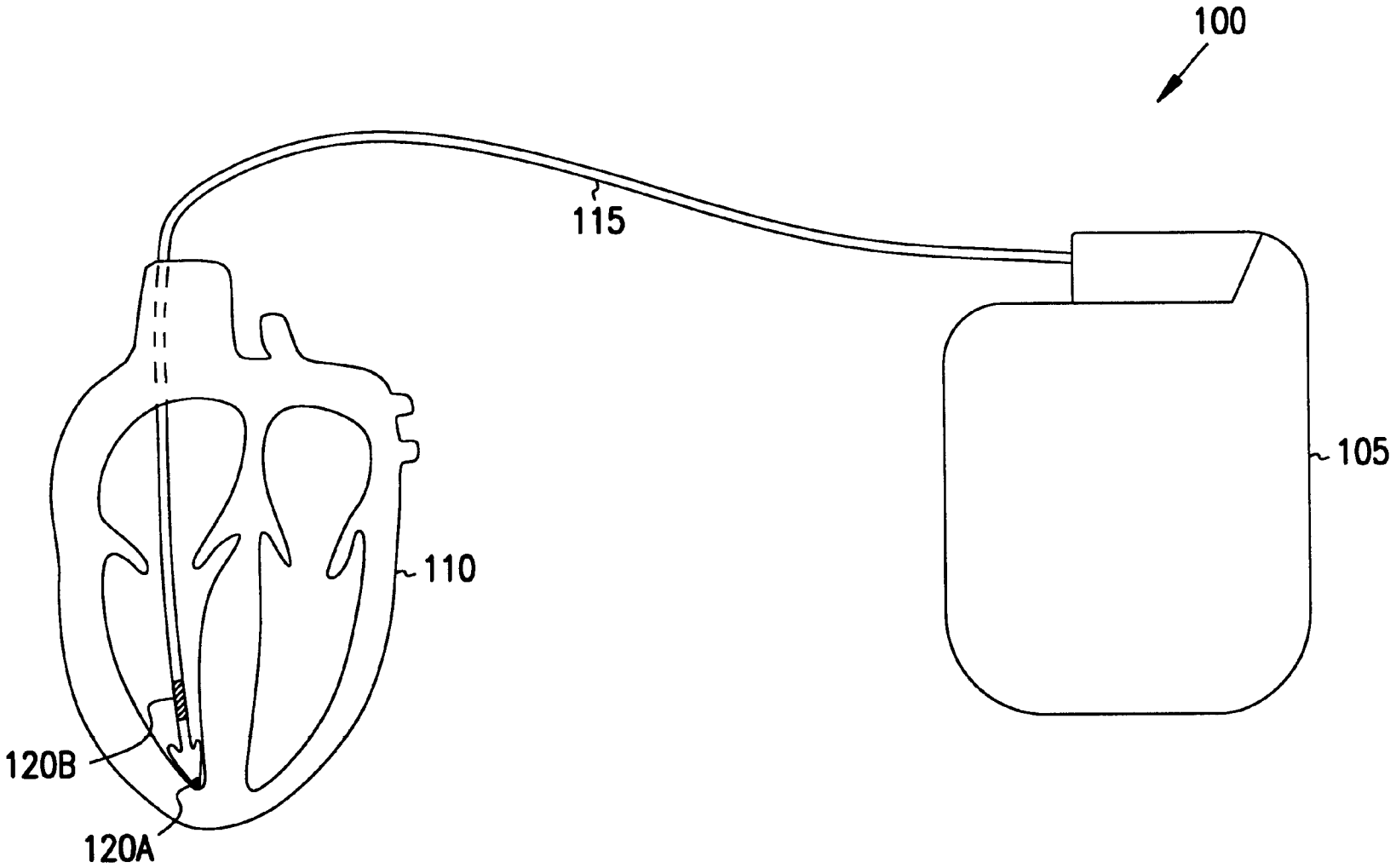
FIG. 1 is a schematic diagram illustrating generally a cardiac rhythm management device and an environment in which it is used.

In the drawings that accompany the following detailed description, like numerals describe substantially similar components throughout the several views.

System Overview

This document describes a cardiac rhythm management system including a lead impedance measurement system. FIG. 1 is a schematic diagram illustrating a cardiac rhythm management system 100 including a cardiac rhythm management device 105 coupled to a heart 110 via a leadwire 115. Leadwire 115 includes electrodes, such as tip electrode 120A and ring electrode 120B for delivering bipolar pacing pulses therebetween.

Figure 2:
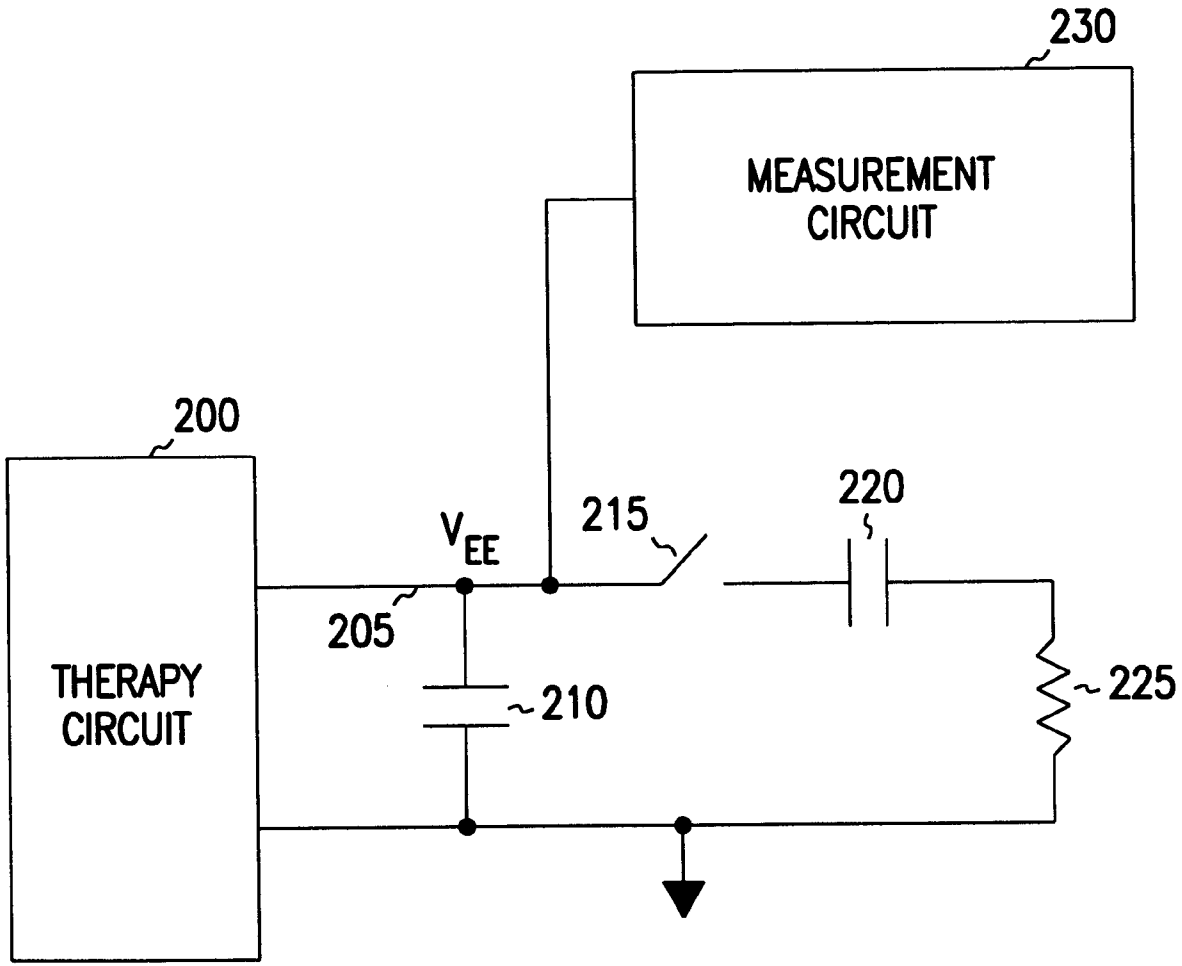
FIG. 2 is a schematic/block diagram illustrating a portion of a cardiac rhythm management device in more detail.

FIG. 2 illustrates a portion of device 105 in more detail. Device 105 includes a therapy circuit 200 that generates a pacing voltage $V_{EE}$ at node 205. The pacing voltage $V_{EE}$ is stored across a storage capacitor 210 for delivering pacing pulses to heart 110 through a pacing switch 215 and a coupling capacitor 220. In FIG. 2, resistance 225 represents the lead impedance seen by device 105. Resistance 225 includes the impedance of leadwire 115 in series with the impedance of the heart tissue and body fluids between tip electrode 120A and ring electrode 120B. A lead impedance measurement circuit 230 is coupled to receive the pacing voltage $V_{EE}$ at node 205.

Lead Impedance Measurement Circuit

Figure 3:
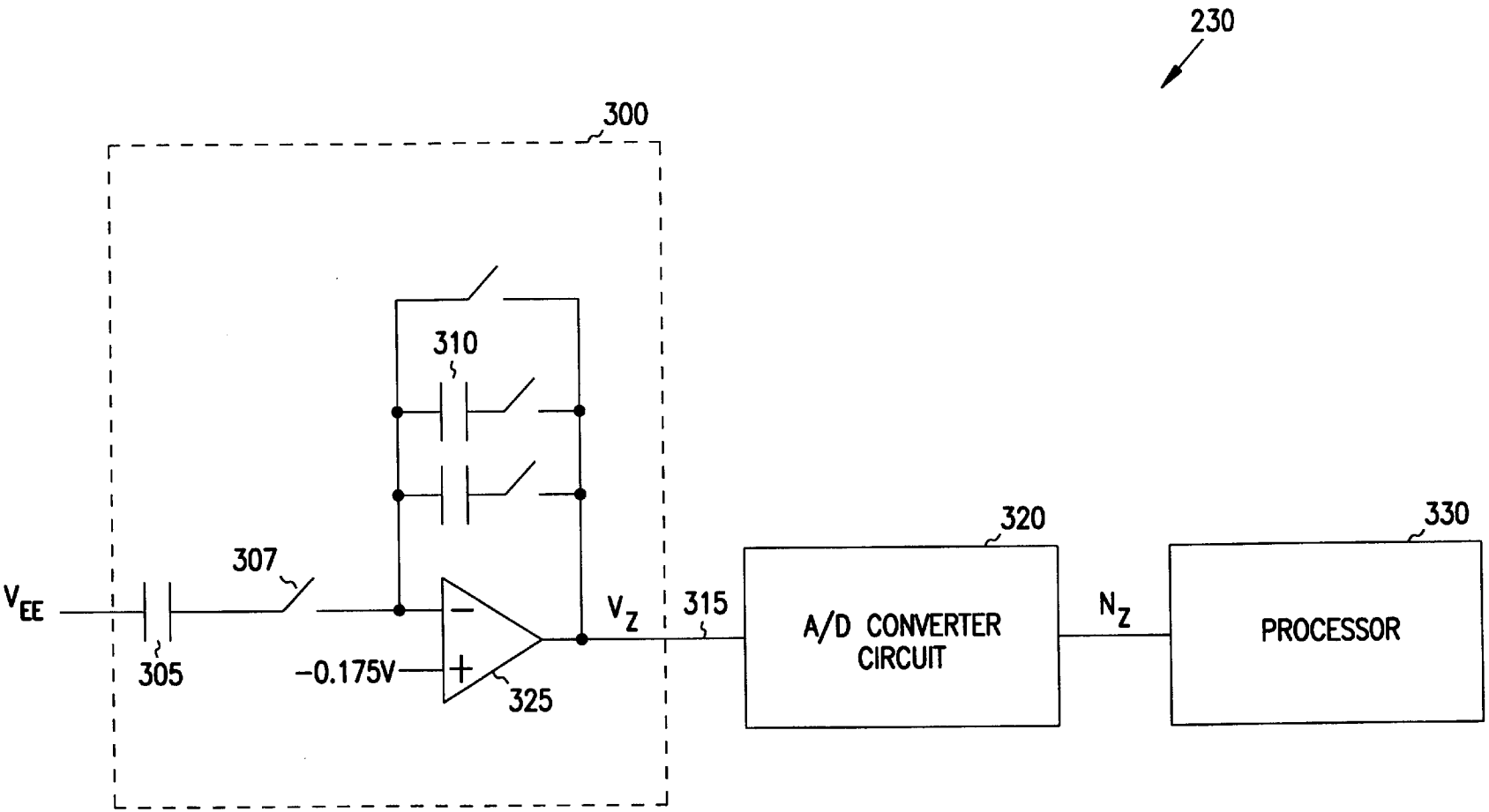
FIG. 3 illustrates portions of a lead impedance measurement circuit.

FIG. 3 illustrates portions of lead impedance measurement circuit 230 in more detail. In FIG. 3, the pacing voltage $V_{EE}$ is received by a switched-capacitor gain circuit 300 (in this document, "gain" is understood to refer also to attenuation). Gain circuit 300 includes input capacitor 305 and feedback capacitor 310. Switch 307 is turned on at the beginning of a pacing pulse and is turned off after a fixed time period that is shorter than duration of the pacing pulse. Gain circuit 300 provides an output voltage $v_z$ at node 315 that is received at the input of analog-to-digital (A/D) converter 320. A/D converter 320 converts the voltage $v_Z$ into a digital value $n_Z$, which is provided to a processor 330 for carrying out calculations for obtaining the desired lead impedance, as described below.

Method of Using Lead Impedance Measurement Circuit

Figure 4:
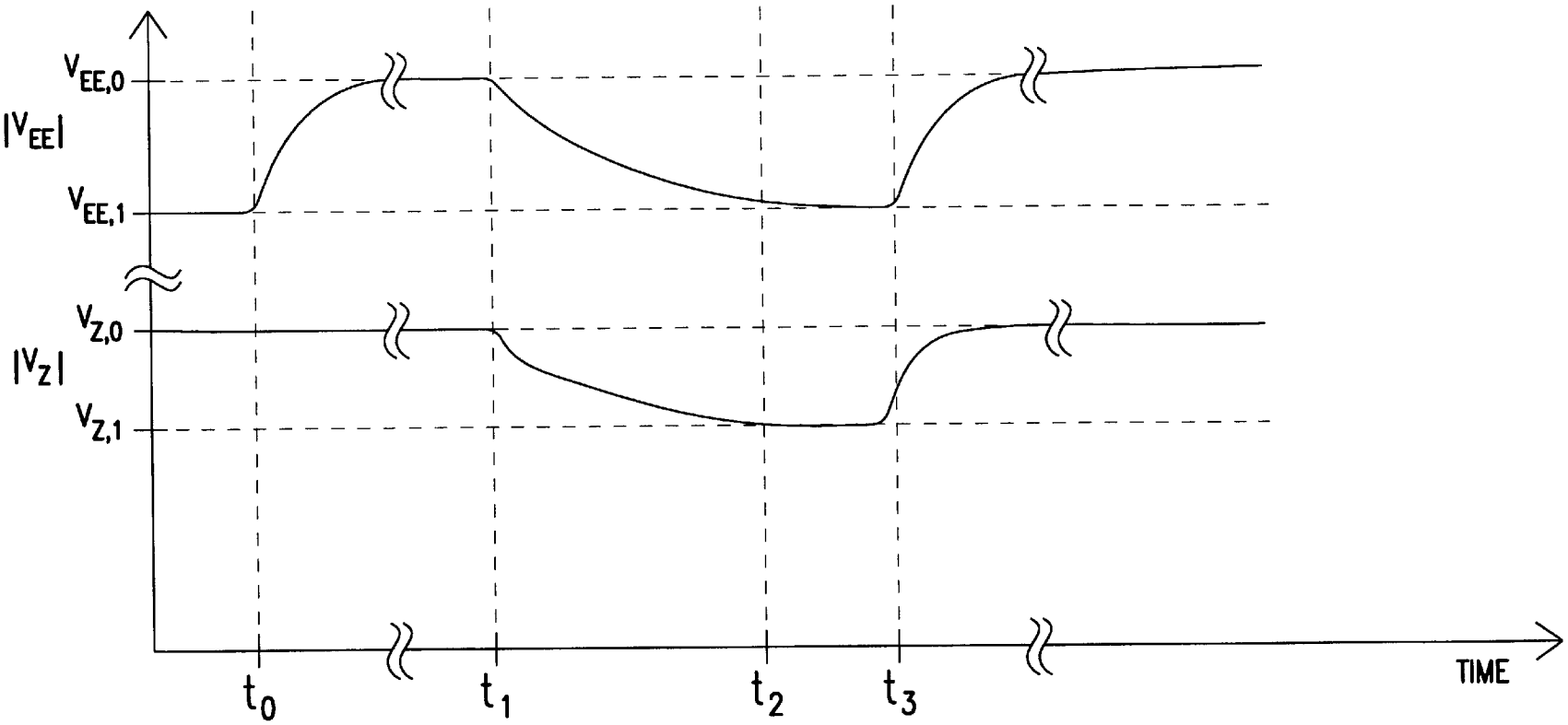
FIG. 4 is a signal graph illustrating generally the magnitude of a pacing voltage $V_{EE}$ and the magnitude of an output voltage $v_z$ of a gain circuit as a function of time.

FIG. 4 is a signal graph illustrating the magnitude of pacing voltage $V_{EE}$ and the magnitude of output voltage $v_z$ of gain circuit 300 as a function of time. At time $t_0$, therapy circuit 200 begins charging node 205 toward the programmed acing voltage $V_{EE,0}$. At time $t_1$, pacing switch 215 closes, discharging storage capacitor 210 through coupling capacitor 220 and resistance 225. In FIG. 4, the magnitude of the pacing voltage $V_{EE}$ accordingly begins to change, drooping from $V_{EE,0}$ as storage capacitor 210 is being discharged during delivery of the pacing energy. At time $t_3$, pacing switch 215 opens, and the pacing voltage $V_{EE}$ in FIG. 4 has drooped to $V_{EE,1}$. After time $t_3$, therapy circuit 200 begins recharging storage capacitor 210 toward the programmed pacing voltage $V_{EE,0}$. Before time $t_1$, the output voltage $v_z$ of gain circuit 300 is held at a reference potential, such as by autozeroing (i.e., closing the feedback loop around) operational amplifier 325. Between time $t_1$ and $t_2$, the output voltage $v_z$ tracks the droop of pacing voltage $V_{EE}$. At time $t_2$, the output voltage $v_{z1}$ provides to A/D converter 320 a measured indication of the droop of pacing voltage $V_{EE}$. The A/D converter 320 converts the output voltage $v_{z1}$ to the digital value $n_z$, from which an indication of the lead impedance can be obtained. After time $t_3$, the output voltage $v_z$ of gain circuit 300 is held at a reference potential, such as by autozeroing operational amplifier 325.

Figure 5:
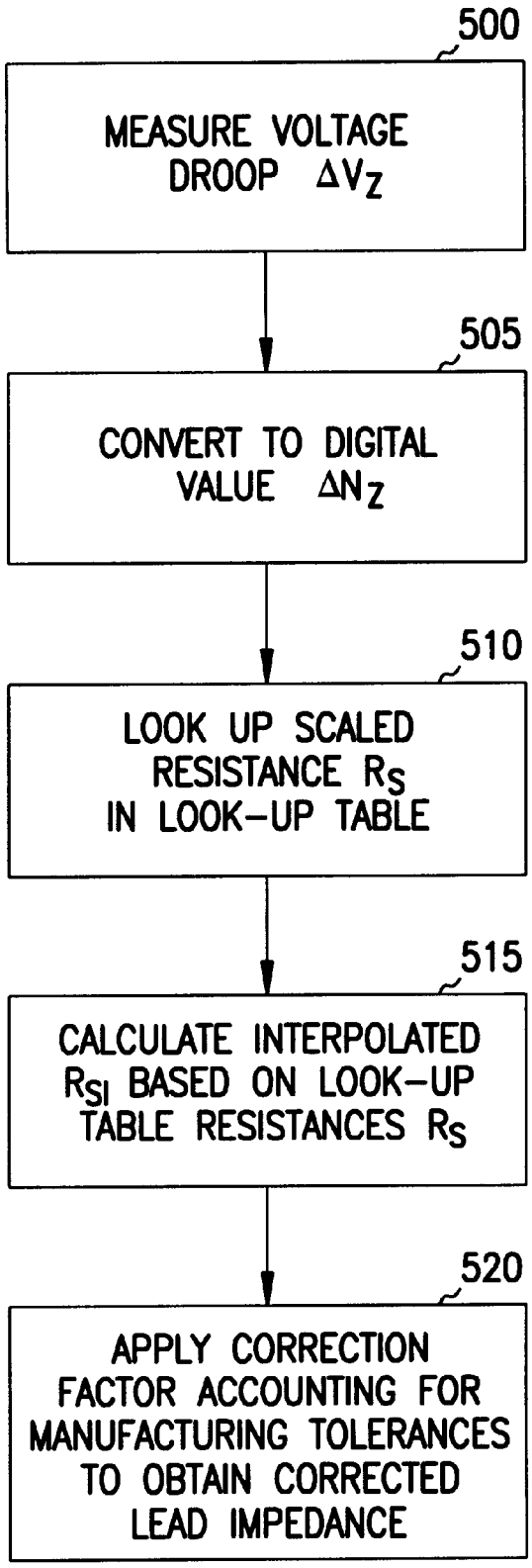
FIG. 5 is a flow chart illustrating generally one method of using a cardiac rhythm management system and a lead impedance measurement circuit to obtain lead impedance measurements.

FIG. 5 is a flow chart illustrating using system 100 and lead impedance measurement circuit 230 to obtain lead impedance measurements. At step 500,system 100 provides a measurement at node 315 of a voltage droop, $\Delta v_z$, that is based on the voltage droop of pacing voltage $V_{EE}$ during issuance of a pacing pulse. At step 505, the voltage droop measurement at node 315 is converted to a digital value, $\Delta n_z$, at the output of A/D converter 320. At step 510, system 100 looks up a scaled resistance, $R_s$, in a look-up table. At step 515, an interpolated resistance $R_{si}$ is calculated based on adjacent values of the scaled resistance $R_s$ in the look-up table. At step 520, a correction factor is applied to the interpolated resistance $R_{si}$ to account for manufacturing tolerances, resulting in a corrected lead impedance measurement $R_{sic}$.

Voltage Droop Calculations

Equation 1 describes the change in output voltage droop $\Delta v_z$ at node 315 from a particular programmed pacing voltage $V_{EE,0}$ during the time period that pacing switch 215 is closed.

$$\Delta v_z = -\frac{C_{305}}{C_{310}} \cdot \frac{C_{220}}{(C_{210} + C_{220})} \cdot V_{EE,0} \cdot \left(1 - e^{-\frac{t}{R_{225} \cdot C}}\right) \tag{1}$$

In Equation 1, $C_{210}$, $C_{220}$, $C_{305}$, and $C_{210}$ are the capacitance values of storage capacitor 210, coupling capacitor 220, input capacitor 305, and feedback capacitor 310, respectively. $R_{225}$ is the lead impedance value of resistance. $V_{EE,0}$ is the programmed pacing voltage. In this document, $C=(C_{210} \cdot C_{220})/(C_{210}+C_{220})$. The fixed time difference $t_2-t_1$, over which the voltage droop is monitored, is represented in Equation 1 by the time, t. The resulting change in voltage $\Delta v_z$ is the voltage droop at node 315.

Equation 2 represents the value $R_{225}$ of lead resistance 225 obtained by solving Equation 1, and making an appropriate substitution for the change in the digital value, $\Delta n_z$, at the output of A/D converter 320.

$$R_{225} = -\frac{t}{C \cdot \ln\left(1 - \Delta n_z \cdot \frac{0.7}{256} \cdot \frac{C_{310}}{C_{305}} \cdot \frac{1}{K_c \cdot V_{EE,0}}\right)} \tag{2}$$

In Equation 2, $K_c=C_{220}/(C_{210}+C_{220})$, and the factor 0.7/256 represents the input voltage range of A/D converter 320 of 0.7 Volts, divided by its quantized resolution, which, in this case, is 256 steps for an 8-bit A/D converter 320. The gain of gain circuit 300 is adjusted, along with the programmed pacing voltage $V_{EE,0}$ and the duration, t, of the lead impedance measurement ($t=t_2-t_1$), to ensure adequate voltage droop $\Delta v_z$ at node 315 over the range of impedance to be measured (e.g., 100 to 2500 ohms).

Lookup Tables and Scaling

Equation 2 requires a natural logarithm function, ln(), which is difficult to perform in a typical microcontroller in an implanted cardiac rhythm management device 105. As a result, while Equation 2 is appropriate for determining the lead impedance value $R_{225}$ in an external programmer, it is difficult to use Equation 2 within an implanted cardiac rhythm management device 105 to determine the lead impedance value $R_{225}$. One aspect of the invention avoids using the natural logarithm function, ln(), of Equation 2 by using instead at least one lookup table. A lookup table is easier to implement on processor 330 within implanted cardiac rhythm management device 105 than a natural logarithm function, ln().

Tables 1 and 2 illustrate examples of such look-up tables, which are suitable for implementation on processor 330 within cardiac rhythm management device 105.

TABLE 1

Lookup Table for Nominal Pacing Conditions ($V_{EE,0}$ = 3.5 V, $t_3 - t_1$ = 0.35 milliseconds), Gain = 0.60.

| Index | $\Delta n_z$ (counts) | $R_s$ (counts) |
|---|---|---|
| 0 (lower) | 9 | 237 |
| 1 | 15 | 141 |
| 2 | 27 | 77 |
| 3 | 47 | 43 |
| 4 | 81 | 24 |
| 5 | 130 | 14 |
| 6 | 190 | 9 |
| 7 (upper) | 255 | 11 6 |

TABLE 2

Lookup Table for Default Lead Impedance Measurement Conditions ($V_{EE,0}$ = 5.0 V, $t_3 - t_1$ = 0.35 milliseconds), Gain = 0.45.

| Index | $\Delta n_z$ (counts) | $R_S$ (counts)j |
|---|---|---|
| 0 (lower) | 9 | 254 |
| 1 | 16 | 142 |
| 2 | 28 | 80 |
| 3 | 50 | 44 |
| 4 | 85 | 25 |
| 5 | 140 | 14 |
| 6 | 190 | 10 |
| 7 (upper) | 245 | ‘7 |

Tables 1 and 2 correlate the digitized voltage droop $\Delta n_z$ output from A/D converter 320 to a scaled resistance, $R_S$, measured in counts, which is an 8-bit representation of $R_{225}$ (i.e., scaled to 12 ohms per count). The scaled resistances, $R_S$, in Tables 1 and 2 are generated using Equation 2 to obtain an ideal value of $R_{225}$. Then, these ideal values of $R_{225}$ are scaled using Equation 3 to obtain the scaled resistances, $R_S$, in Tables 1 and 2.

$$R_S = integer\left(\frac{0.96 \cdot R_{225} + \frac{\Omega q}{2}}{\Omega q}\right) \tag{3}$$

In Equation 3, $R_{225}$ is obtained using Equation 2, $\Omega_q$ is the scaling factor of 12 ohms per count. The percentage multiplier of 0.96 more closely matches the logarithmic ideal curve of lead impedance to the piecewise linear approximation imposed by the finite and limited number of values (e.g., 8 values) of $R_{225}$ included each of Tables 1 and 2. The percentage multiplier allows the error of the piecewise linear approximation to be distributed both positive and negative about the ideal lead impedance curve, thereby reducing the absolute error over most of the impedance measurement range to less than approximately +/−5%. The integer function rounds the resulting scaled resistance value, $R_S$, to an 8-bit integer value, as illustrated in Tables 1 and 2.

Interpolation

Because only eight values of are provided in each of Tables 1 and 2, system 100 uses an interpolation technique to obtain scaled resistances $R_S$ that correspond to measured values of $\Delta n_z$ falling between the values of $\Delta n_z$ that are listed in Tables 1 and 2. One approach of performing the interpolation is illustrated by Equation 4.

$$R_{si} = integer\left[R_{sl} + \frac{R_{su} - R_{sl}}{\Delta n_{zu} - \Delta n_{zl}} \cdot (\Delta n_z - \Delta n_{zl}) + 0.5\right] \tag{4}$$

In Equation 4, $\Delta n_z$ is a measured value that may fall between upper and lower $\Delta n_z$ values listed, and corresponding upper and lower $R_s$ values, listed in Tables 1 and 2. In Equation 4, $\Delta n_{z1}$ is the lower table value, $\Delta n_{zu}$ is the upper table value, $R_{su}$ is the upper table value, $R_{s1}$ is the lower table value, and $R_{si}$ is the resulting interpolated value of the resistance scaled from $R_{225}$.

Correction for Manufacturing Tolerances

In manufacturing a plurality of devices 105, the capacitance values of storage capacitor 210 and coupling capacitor 220, and the switch resistance value of pacing switch 215 may all vary from a particular one of devices 105 to a different one of devices 105 due to the manufacturing variations in these components from their nominal values. Because Equations 1 and 2 used the nominal values of these components, system 100 allows a correction to be made for such manufacturing variations as described below.

First, known resistances values $R_{z1}$=200 Ω and $R_{z2}$=1000 Ω of resistance 225 are measured by system 100 according to the techniques described above, obtaining resulting measured values $\Delta n_{z1}$ and $\Delta n_{z2}$.

$$K_x = -\frac{1}{\ln\left(1 - \Delta n_z \cdot \frac{0.7}{256} \cdot \frac{C_{310}}{C_{350}} \cdot \frac{1}{K_c \cdot V_{EE,0}}\right)} \tag{5}$$

Equation 5 is similar to Equation 2, except the result $K_x$ is scaled from $R_{225}$ by a constant factor (i.e., $K_x=(C \cdot R_{225}) \div t$). Equation 5 results in $K_1$, and $K_2$, corresponding to $\Delta n_{z1}$ and $\Delta n_{z2}$, respectively. Next, Equation 6 is applied to the values $K_1$ and $K_2$ obtained from Equation 5 to obtain an offset correction factor ΔR.

$$\Delta R = \frac{K_1 \cdot R_{z2} - K_2 \cdot R_{z1}}{K_2 - K_1} \tag{6}$$

Then, the offset correction factor ΔR is scaled according to Equation 7, to obtain a scaled offset correction factor $\Delta R_s$.

$$\Delta R_s = \frac{\Delta R}{\Omega q} - 0.5 \quad (7)$$

Furthermore, a slope correction factor, SCF, is obtained using Equation 8.

$$SCF = \frac{C \cdot (R_{z2} - R_{z1})}{-t \cdot (K_2 - K_1)} \quad (8)$$

Next, using Equation 9, the slope correction factor, SCF, and the scaled offset correction factor, $\Delta R_s$, are applied to the interpolated measured lead resistances $R_{si}$, obtained by system 100 from Equation 4. This results in the corrected measured lead resistance $R_{sic}$.

$$R_{sic} = integer(R_{si} \cdot SCF - \Delta R_s) \quad (9)$$

The corrected measured lead impedance is converted to ohms by multiplying it by the scaling factor Ωq of 12 ohms per count. System 100 provides a measured lead impedance of greater than approximately +/−20% accuracy and 5% precision over a resistance range of 100 Ω to 2500 Ω.

What is claimed is:

1. An implantable cardiac rhythm management system comprising:

a cardiac rhythm management device adapted for being implanted in a living organism;

a leadwire, coupled to the device, and providing at least one electrode;

a therapy circuit, coupled to the leadwire for providing electrical energy to the living organism;

a lead impedance measurement circuit, coupled to the leadwire and the therapy circuit, and providing an indication of a resistance of the leadwire based on a measured change in voltage resulting from the electrical energy provided to the living organism, wherein the lead impedance measurement is based on a predetermined set of resistances corresponding to a predetermined set of changes in voltage to which the measured change in voltage is compared;

an interpolation circuit providing a lead impedance measurement interpolated from values in the predetermined set of resistances and the predetermined set of changes in voltage; and a correction factor circuit that is capable of adjusting the lead impedance measurement based on component variations from a nominal value in the device.

* * * * *